United States Patent [19]

Zimmerman

[11] 4,141,894
[45] Feb. 27, 1979

[54] TRANS-5A-ARYL-DECAHYDROBENZAZE-PINES

[75] Inventor: Dennis M. Zimmerman, Mooresville, Ind.

[73] Assignee: Eli Lilly and Company, Indianapolis, Ind.

[21] Appl. No.: 737,959

[22] Filed: Nov. 2, 1976

[51] Int. Cl.² ............................................ C07D 223/16
[52] U.S. Cl. ........................ 260/239 BB; 260/239 BB; 260/346.22; 424/244
[58] Field of Search ................................ 260/239 BB

[56] References Cited

U.S. PATENT DOCUMENTS

| 4,001,247 | 1/1977 | Zimmerman et al. ............ 260/289 D |
| 4,001,248 | 1/1977 | Zimmerman et al. ............ 260/289 D |

FOREIGN PATENT DOCUMENTS 802557  11/1973  Belgium .............................. 260/289 D

*Primary Examiner*—Donald G. Daus
*Assistant Examiner*—D. B. Springer
*Attorney, Agent, or Firm*—Charles W. Ashbrook; Everet F. Smith

[57] ABSTRACT

Trans-5a-phenyl (and substituted phenyl)-N-substituted-2,3,4,5,5a,6,7,8,9,9a-decahydro-1H-2 and 1H-3-benzazepines are useful as analgesic drugs displaying mixed narcotic agonist and antagonist activity.

27 Claims, No Drawings

TRANS-5A-ARYL-DECAHYDROBENZAZEPINES

BACKGROUND OF THE INVENTION

Morphine is the natural alkaloid which gives opium its analgesic action. It has been known and used for centuries and still today is the standard against which new analgesics are measured. Extensive chemical modifications of morphine have produced analgesic substances of widely differing potency and addictive properties. Codeine, for example, the methyl ether of morphine, is a mild analgesic with only slight physical dependance liability. In contrast, the diacetyl derivative of morphine, heroin, is a powerful analgesic agonist with extremely high physical dependance liability. In addition to morphine and codeine, there are many other semisynthetic or totally synthetic derivatives and structures of opium type alkaloids, entailing several structurally distinct chemical classes of drugs displaying pharmacological properties related to those of morphine. Clinically useful drugs of this type include the morphinans, benzomorphans, methadones, phenylpiperidines, and propionanilides.

Recently several new drugs have been synthesized which have both analgesic agonist and antagonist properties with varying degrees of physical dependance liabilities. These new drugs in some cases can be viewed as morphine part-structures. For example, certain decahydroisoquinolines having a hydroxyphenyl group attached at the ring junction para to the isoquinoline nitrogen atom can be viewed as a morphine part-structure. Such compounds are the subject of Belgian Pat. No. 802,557.

An object of this invention is to provide certain N-substituted-5a-aryl-decahydrobenzazepines which can be viewed as being somewhat structurally related to certain morphine part-structures such as the aforementioned morphinans, benzomorphans, and isoquinoline derivatives. The compounds provided by this invention have not heretofore been described, as no method for their preparation has been available. Additionally, the compounds of this invention display an unpredictable variation in analgesic antagonist and agonist properties, but usually (invariably) with decreased physical dependance liability.

SUMMARY OF THE INVENTION

This invention provides bicyclic analgesic compounds characterized as decahydrobenzazepine derivatives. More particularly, the invention provides trans-5a-aryl-decahydro-1H-2 and 1H-3-benzazepines represented by the generallized structural formula

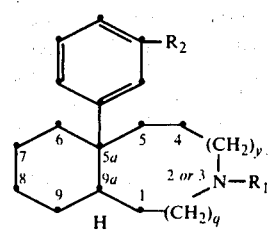

in which one of y and q is zero and the other is 1; $R_1$ is hydrogen, $C_1$-$C_8$ alkyl, $CH_2R_3$ or

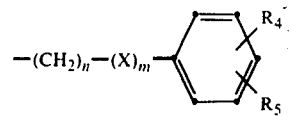

in which $R_3$ is $C_2$-$C_7$ alkenyl, $C_3$-$C_6$ cycloalkyl, furyl, or tetrahydrofuryl; X is CO, CHOH, CH=CH, S or O; n is 0, 1, 2 or 3, m is 0 or 1, except that when m is 0, n is other than O, and when n is 0, X is other than S or O; $R_4$ and $R_5$ independently are hydrogen, $C_1$-$C_3$ alkyl, or halogen; and $R_2$ is hydrogen, hydroxy, $C_1$-$C_3$ alkoxy, or $C_1$-$C_3$ alkanoyloxy. Also included within the scope of this invention are the non-toxic pharmaceutically acceptable acid addition salts of the benzazepine derivatives having the above formula. Additionally encompassed within the scope of this invention are intermediate compounds having the above formula wherein

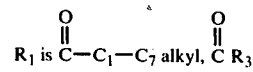

in which $R_3$ has the above-defined meanings, and

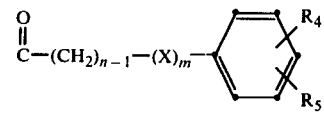

in which n, m, X, $R_4$ and $R_5$ have the above defined meaning.

A preferred group of compounds comprehended by this invention are those having the above formula when $R_1$ is alkyl or $CH_2R_3$ when $R_3$ is alkenyl or cycloalkyl. Also preferred are those compounds of the above formula when $R_2$ is hydrogen, hydroxy, or alkoxy. An especially preferred group of compounds are those of the above formula wherein $R_1$ is hydrogen, methyl, or benzyl, and $R_2$ is methoxy or hydroxy.

DETAILED DESCRIPTION OF THE INVENTION

The compounds provided by this invention represented by the above formula are named as benzazepine derivatives. Those compounds having the above formula wherein y is 1 and q is zero are named as 1H-2-benzazepine derivatives, since the nitrogen atom is located at the 2-position of the bicyclic ring system. Those compounds having the above formula wherein y is zero and q is 1 are referred to as 1H-3-benzazepines, since the nitrogen atom is located at the 3-position of the molecule. All of the compounds provided by this invention are totally saturated in the bicyclic ring system, and consequently the compounds are named as decahydrobenzazepines, specifically as 2,3,4,5,5a,6,7,8,9,9a-decahydro-1H-2-benzazepines and as 2,3,4,5,5a,6,7,8,9,9a-decahydro-1H-3-benzazepines. All of the compounds of this invention are decahydrobenzazepine derivatives which bear an aryl substituent at the 5a-position of the bicyclic ring system. As indicated in the above formula, such 5a-aryl moiety is a phenyl group or a phenyl group which is itself substituted at it's 3-position. A further aspect of the compounds of this invention is that such decahydrobenzazepines have two asymmetric carbon atoms within the bicyclic ring system; namely, the 5a carbon atom and the 9a carbon atom. Both are asymmetric centers. As a consequence, such compounds can exist as four stereoisomers, or as two racemic or dl-pairs. This invention provides the decahydrobenzazepines having the above formula wherein the 5a-aryl group is oriented on the opposite side of the plane of the molecule from the 9a-hydrogen atom. Such compounds are designated as trans-isomers. This invention accordingly comprehends the pharmacologically active individual optically-active trans isomers, in addition to the racemic mixture of trans isomers. Such racemic pair of trans-decahydrobenzazepines can be separated into its component stereoisomers by procedures well known in the art. In the event that all useful pharmacologic activity resides in one stereoisomer, the dl-racemate is still useful in that it contains, as a constituent part, the pharmacologically active isomer.

The compounds of this invention are named according to standard procedures including the designation of stereochemistry, points of saturation, and substitution. For example, the compound of the above formula in which q is zero and y is 1, $R_1$ is methyl and $R_2$ is methoxy, is named as trans-dl-2-methyl-5a-(3-methoxyphenyl)-2,3,4,5,5a,6,7,8,9,9a-decahydro-1H-2-benzazepine.

As used throughout the present specification and in the appended claims, the term "$C_1$-$C_8$ alkyl" as defined by $R_1$ in the above formula refers to both straight and branched carbon chains such as methyl, ethyl, n-propyl, n-pentyl, isopropyl, n-butyl, 1-methylbutyl, 2-ethylpentyl, n-hexyl, 3-ethylhexyl, 1,1-dimethylhexyl, 1,2-dimethylpentyl, 1,2,3-trimethylbutyl, 1-ethylhexyl, n-octyl, isooctyl, and related groups. $R_1$ is also defined as $CH_2R_3$ wherein $R_3$ is $C_2$-$C_7$ *alkenyl*, $C_3$-$C_6$ cycloalkyl, furyl or tetrahydrofuryl. Examples of such $R_1$ groups thus include 2-propenyl or allyl, 3-butenyl, 2-methyl-2-pentenyl, 2,2-dimethyl-3-hexenyl, 3-ethyl-2-pentenyl, 3-methyl-4-heptenyl, 4-ethyl-2-hexenyl, 5-heptenyl, 2-methyl-4-heptenyl, cyclopropylmethyl, cyclobutylmethyl, cyclopentylmethyl, cyclohexylmethyl, 2-furylmethyl, 2-tetrahydrofurylmethyl, and 3-tetrahydrofurylmethyl. $R_1$ is also defined as a group of the formula

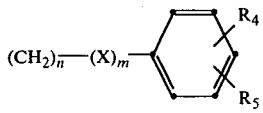

in which n is 0, 1, 2, or 3; m is 0 or 1; X is CO, CHOH, CH=CH, S or O, except that when m is 0, n is other than O, and when n is 0, X is other than S or O; and $R_4$ and $R_5$ independently are hydrogen, $C_1$-$C_3$ alkyl, or halogen. The term halogen as used herein includes fluorine, bromine, chlorine and iodine. $C_1$-$C_3$ alkyl groups include methyl, ethyl, n-propyl and isopropyl. Representative examples of $R_1$ defined by the above formula include benzyl, 2-phenylethyl, 2-(3,4-dichlorophenyl)ethyl, 3-(2-methyl-5-ethylphenyl)propyl, benzoylmethyl, 2-(4-fluorophenylcarbonyl)ethyl, phenoxymethyl, 2-(3-chloro-4-ethylphenoxy)ethyl, phenylthiomethyl, 2-(4,5-dimethylphenyl)-2-hydroxyethyl, 2-(2,6-diiodophenylthio)ethyl, 3-(3-bromophenylthio)propyl, 3-phenyl-2-propenyl, and related groups.

In accordance with this invention, the decahydrobenzazepines represented by the above formula are synthesized utilizing a somewhat lengthy reaction path, starting with readily available 2-arylcyclohexanones such as 2-phenylcyclohexanone, 2-(3-methoxyphenyl)cyclohexanone, 2-(3-ethoxyphenyl)cyclohexanone, and the like. In this synthetic procedure, a 2-arylcyclohexanone is first converted to a 10-aryl-$\Delta^1$-2-octalone by the Michael condensation with 1-(N,N-diethylamino)-3-butanone in the presence of a condensing agent such as sodium hydride. Such condensation was first reported by Boekelheide, J. Am. Chem. Soc., 69, 798 (1947), who reported the synthesis of 10-phenyl-$\Delta^1$-2-octalone. Reduction of the $\Delta^1$-double bond of such 10-aryl-$\Delta^1$-2-octalones provides exclusively a 4a-aryl-2-decalone of the transconfiguration. For example, reduction of 10-phenyl-$\Delta^1$-2-octalone by reaction with lithium in liquid ammonia affords exclusively trans-dl-4a-phenyl-2-decalone. Such reaction may additionally effect minor reduction of the decalone carbonyl group to afford minor quantities of the corresponding trans-dl-4a-aryl-2-decalol. The product of reduction of the aforementioned octalone derivative, including both decalone and decalol, can be subjected to oxidation utilizing Jones reagent (ie, chromic oxide in concentrated sulfuric acid), thereby smoothly yielding a unitary product, namely a trans-dl-4a-aryl-2-decalone. Decalone derivatives commonly prepared according to this procedure include trans-dl-4a-(3-methoxyphenyl)-2-decalone, trans-dl-4a-(3-ethoxyphenyl)-2-decalone, and trans-dl-4a-(3-isopropoxyphenyl)-2-decalone.

The trans-dl-4a-aryl-2-decalones thus prepared are next converted to the corresponding oxime by reaction with hydroxylamine under standard reaction conditions. For example, a decalone derivative such as trans-dl-4a-(3-ethoxyphenyl)-2-decalone can be reacted with an equimolar quantity or an excess of hydroxylamine, generally as the hydrochloride salt, in the presence of a base such as sodium bicarbonate or pyridine, and in a solvent such as methanol, ethanol, water, dioxane, or the like. The reaction generally is carried out at a temperature of about 50° to about 150° C., and usually is complete within 4 to 8 hours. The decalone oxime product, ie. the trans-dl-4a-aryl-2-decalone oxime, is readily isolated by extraction into a solvent such as diethyl ether, and evaporation of the solvent from such extract. Further purification of such oxime is normally not required.

The trans-dl-4a-aryl-2-decalone oximes so formed are next subjected to standard Beckmann rearrangement conditions, thereby effecting ring expansion to form a 5,7-bicyclic ring system. For example, a decalone derivative such as trans-dl-4a-phenyl-2-decalone oxime can be reacted with an acid, for instance polyphosphoric acid or the like, at a temperature of about 100° to 150° C. for a period of time of about ½ to 2 hours, thus effecting ring expansion at the oxime position. As would be expected, since the oxime exists in both possible steric configurations, such ring expansion follows two paths, in that the expansion can take place by cleavage of the decalone $C_1$-$C_2$ bond, or alternatively cleavage of the decalone $C_2$-$C_3$ bond. The product of such ring expansion reaction is thus a mixture of trans-dl-4a-aryl-2-benzazepine derivatives and 3-benzazepine derivatives. Such benzazepine derivatives are cyclic amides in that the 2-benzazepines have a carbonyl group at the C-3 position, while the 3-benzazepines have a carbonyl group at the C-2 position. Such mixture of benzazepine derivatives can be depicted by the following generalized formulas:

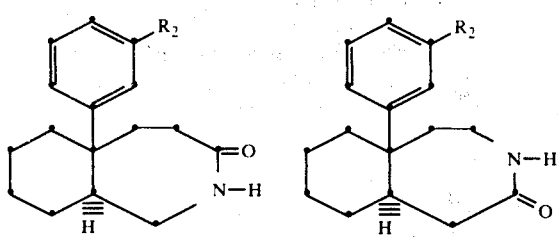

wherein $R_2$ has the above-defined meaning, but is preferably hydrogen or $C_1$-$C_3$ alkoxy, particularly methoxy, for the reasons discussed hereinbelow. Such cyclic amides are accordingly named trans-dl-5a-phenyl-(or substituted phenyl)-3-oxo-2,3,4,5,5a,6,7,8,9,9a-decahydro-1H-2-benzazepines and trans-dl-5a-phenyl-(or substituted phenyl)-2-oxo-2,3,4,5,5a,6,7,8,9,9a-decahydro-1H-3-benzazepines.

The mixture of benzazepine derivatives so formed is preferably not separated at this point but rather is next derivatized at the amide nitrogen position. For example, such mixture of 3-oxo-2-benzazepines and 2-oxo-3-benzazepines can be alkylated by reaction with an alkylating agent in the presence of a base to provide the corresponding 2-substituted-3-oxo-2-benzazepine and 3-substituted-2-oxo-3-benzazepine derivatives as a mixture. Commonly used alkylating agents are those having the formula $R_1'$-B, in which $R_1'$ is a subgroup of the above-defined $R_1$, and includes $C_1$-$C_8$ alkyl, $CH_2R_3$, in which $R_3$ is $C_2$-$C_7$ alkenyl, $C_3$-$C_6$ cycloalkyl, furyl, and tetrahydrofuryl, as well as aralkyl groups such as benzyl, 2-phenylethyl, 3-(3,4-dichlorophenyl)propyl, and the like. B is defined as any of a number of good leaving groups, such as halogen, for instance chloro, bromo, or iodo, as well as para-toluenesulfonyl (tosyl), para-bromotoluenesulfonyl, methanesulfonyl, azido, quaternized amino, and the like. Preferred alkylating agents are those having the formula $R_1'$-B in which B is halogen, especially chlorine or bromine, and tosyl. It is additionally preferred that the alkylating agents utilized include those compounds in which $R_1'$ is lower alkyl or lower alkenyl such as methyl, ethyl, n-propyl, n-butyl, isopentyl, allyl, 3-butenyl, 2-methyl-3-pentenyl, and the like, as well as cycloalkylmethyl groups such as cyclopropylmethyl, cyclobutylmethyl, and cyclopentylmethyl. An additionally preferred alkylating agent is one in which $R_1'$ is benzyl, 2-phenylethyl, or 3-phenylpropyl. The most preferred alkylating agents used to alkylate the aforementioned mixture of oxo-benzazepine derivatives are those compounds wherein $R_1'$ is methyl or benzyl, since such groups can be easily removed at a later stage to provide the decahydrobenzazepines of this invention which are unsubstituted at the nitrogen position; ie. compounds having the above formula wherein $R_1$ is hydrogen, which compounds are useful as intermediates as will be set forth hereinafter.

The alkylation of the above-noted mixture of 3-oxo-2-benzazepine and 2-oxo-3-benzazepine derivatives is carried out by first forming an alkali metal salt with the cyclic amide nitrogen atoms, and then reacting such alkali metal salt with an alkylating agent. More particularly, the cyclic amides are reacted with a base such as sodium amide, lithium amide, potassium amide, sodium diisopropylamide, lithium cyclopropylamide, potassium cyclohexylamide or the like. Such reaction generally is carried out in a solvent such as toluene, dioxane, tetrahydrofuran, diethyl ether, or related solvents, and normally is conducted at a temperature of about 50° to 200°

C. The cyclic amide-alkali metal salt so formed is generally not isolated, but simply is reacted with an alkylating agent in situ. As an example, a mixture of cyclic amides such as trans-dl-5a-(3-ethoxyphenyl)-3-oxo-2,3,4,5,5a,6,7,8,9,9a-decahydro-1H-2-benzazepine and trans-dl-5a-(3-ethoxyphenyl)-2-oxo-2,3,4,5,5a,6,7,8,9,9a-decahydro-1H-3-benzazepine is reacted with about an equimolar quantity or more of a base such as sodium amide in a solvent such as toluene and at a temperature of about 100° C. for about 3 to 6 hours. The reaction mixture is then cooled, and an alkylating agent, for example n-butyl iodide, is added, and the mixture is again heated at a temperature of about 50° to 150° C. for about 6 to 12 hours. The product is, as would be expected, a mixture of the corresponding N-alkylated cyclic amides, for instance trans-dl-5a-(3-ethoxyphenyl)-2-(n-butyl)-3-oxo-2,3,4,5,5a,6,7,8,9,9a-decahydro-1H-2-benzazepine and trans-dl-5a-(3-ethoxyphenyl)-3-(n-butyl)-2-oxo-2,3,4,5,5a,6,7,8,9,9a-decahydro-1H-3-benzazepine. Such mixture is readily recovered from the organic reaction mixture by simply washing away any excess base, for instance by washing the reaction mixture with water, and then evaporating the solvent from the purified organic layer. The mixture so formed preferably is not separated, but rather is reduced to form a mixture of the 2- and 3-benzazepine compounds provided by this invention.

More particularly, the mixture of 2-substituted-3-oxo-2-benzazepine derivatives and 3-substituted-2-oxo-3-benzazepine derivatives is reduced, at the 3-oxo and 2-oxo groups respectively, by reaction with a reducing agent such as, preferably, lithium aluminum hydride, or by catalytic hydrogenation. Generally, the reduction is carried out by commingling approximately equimolar quantities or an excess of the mixture of N-substituted cyclic amides and the reducing agent in a solvent such as tetrahydrofuran, diethyl ether, dioxane, or the like. The reaction normally is carried out at about 50° to 150° C., and usually is complete within about 2 to 10 hours. The product is isolated by first destroying any residual reducing agent, for instance by adding an ester such as ethyl acetate to the reaction mixture, coagulating any inorganic salts, separating the organic layer, and then removing the reaction solvent by evaporation. The product is a mixture of compounds provided by this invention, namely a mixture of trans-dl-5a-phenyl (or substituted phenyl)-2-substituted-2,3,4,5,5a,6,7,8,9,9a-decahydro-1H-2-benzazepine and the corresponding 3-substituted-1H-3-benzazepine derivative.

Separation of the mixture of 2-benzazepine and 3-benzazepine derivatives formed as described hereinabove to provide the respective benzazepine components in pure form is preferably carried out next. Such separation of respective 2- and 3-benzazepine derivatives can be accomplished utilizing standard procedures such as solid liquid chromatography, fractional crystallization, or preferably by converting the mixture to an acid addition salt, and permitting one of the benzazepine isomers to selectively crystallize. For example, a mixture of benzazepine derivatives such as trans-dl-5a-phenyl-2-ethyl-2,3,4,5,5a,6,7,8,9,9a-decahydro-1H-2-benzazepine and trans-dl-5a-phenyl-3-ethyl-2,3,4,5,5a,6,7,8,9,9a-decahydro-1H-3-benzazepine can be converted to their respective acid addition salts, for instance their hydrochloride salts, by reaction with an acid (in this instance anhydrous hydrogen chloride) in a solvent such as diethyl ether. The salt which is formed generally is substantially insoluble in the diethyl ether solvent, and is readily recovered by simple filtration to provide a mixture of 2- and 3-benzazepine derivatives as their acid addition salts. The mixture is then dissolved in a suitable solvent such as ethanol, isopropanol, acetone, or the like. The salt of only one of the two benzazepines present generally crystallizes out of solution preferentially over the salt of the other benzazepine. For example, when crystallized from ethanol, trans-dl-5a-phenyl-2-ethyl-2,3,4,5,5a,6,7,8,9,9a-decahydro-1H-2-benzazepine hydrochloride normally crystallizes and can be collected by filtration, thus leaving substantially pure trans-dl-5a-phenyl-3-ethyl-2,3,4,5,5a,-6,7,8,9,9a-decahydro-1H-3-benzazepine hydrochloride dissolved in the filtrate. This second isomer compound can be recovered by simply evaporating the solvent from the filtrate. In either case, if desired the separated salt can be treated with a base such as aqueous sodium hydroxide in order to provide the purified separated benzazepine derivative in the form of the free base. It will of course be recognized that such free base benzazepine derivatives can easily be converted to any other pharmaceutically acceptable acid addition salt by reaction with any suitable organic or inorganic acid, as will be elaborated upon hereinbelow.

It should be recognized that the above-described cyclic amides, that is the mixture of 3-oxo-1H-2-benzazepines and 2-oxo-1H-3-benzazepines, can be reduced prior to derivatization of the nitrogen atom so as to provide a mixture of cyclic amines, which mixture then can be derivatized and separated as desired. Such process is a useful alternative method for preparing the compounds of this invention; however, the preferred method of preparation is that as described hereinabove, namely initial derivatization of the mixture of cyclic amides, followed by reduction and subsequent separation into the respective component isomers. It is further preferred, as hereinbefore suggested, that the mixture of cyclic amides be alkylated with either a methylating agent such as methyl iodide, or a benzylating agent such as benzyl iodide or benzyl bromide. Such derivatization provides, following reduction of the amide carbonyl groups and separation of the respective component isomers, 2-methyl or benzyl-1H-2-benzazepine derivatives and 3-methyl or benzyl-1H-3-benzazepine derivatives. Such compounds are important not only as analgesic drugs, but additionally are useful as intermediates since the N-methyl compounds are readily de-methylated and the N-benzyl derivatives are easily de-benzylated. For example, a compound such as trans-dl-5a-(3-isopropoxyphenyl)-2-methyl-2,3,4,5,5a,6,7,8,9,9a-decahydro-1H-2-benzazepine can be de-methylated by reaction, first with a lower alkyl or an aryl haloformate such as ethyl chloroformate or phenyl chloroformate to form the corresponding carbamate, and then hydrolysis of such carbamate by reaction with an aqueous base such as sodium hydroxide, thus forming the N-unsubstituted benzazepine derivative, for instance trans-dl-5a-(3-isopropoxyphenyl)-2,3,4,5,5a,6,7,8,9,9a-decahydro-1H-2-benzazepine. Such N-demethylation reactions are familiar to those skilled in the art and are elaborated upon by Abdel-Monen et al. in J. Med. Chem. 15, 208 (1972).

Similarly, 2-benzyl-1H-2-benzazepine derivatives and 3-benzyl-1H-3-benzazepine derivatives are readily de-benzylated by established procedures. For example, such de-benzylation can be achieved by catalytic hydrogenation, utilizing common catalysts such as five percent palladium suspended on carbon or the like. For example, trans-dl-5a-phenyl-3-benzyl-2,3,4,5,5a,6,7,8,9-,9a-decahydro-1H-3-benzazepine can be reacted with hydrogen gas in the presence of palladium suspended on carbon in a solvent such as ethanol or ethyl acetate to afford, after isolation, the corresponding N-unsubstituted benzazepine derivative, namely trans-dl-5a-phenyl-2,3,4,5,5a,6,7,8,9,9a-decahydro-1H-3-benzazepine. General N-debenzylation reactions are described by Hartung and Siminoff in Org. Reactions, 7, 277 (1953), and by Leonard and Fiji in J. Am. Chem. Soc, 85, 3719 (1963). Other N-benzyl benzazepines which are readily de-benzylated include trans-dl-5a-(3-methoxyphenyl)-2-benzyl-2,3,4,5,5a,6,7,8,9,9a-decahydro-1H-2-benzazepine and trans-dl-5a-(3-methoxyphenyl)-3-benzyl-2,3,4,5,5a,6,7,8,9,9a-decahydro-1H-3-benzazepine.

The N-unsubstituted benzazepine derivatives of this invention, wherein $R_1$ is hydrogen, and which are prepared either by N-demethylation or N-debenzylation of the corresponding N-substituted benzazepine derivative, or alternatively by simple reduction of the cyclic amide precursor, are extremely important compounds since they serve as intermediates leading to pharmacologically active compounds of this invention. The following list of N-unsubstituted benzazepine derivatives is presented, therefore, to illustrate a number of useful intermediate compounds.

trans-dl-5a-phenyl-2,3,4,5,5a,6,7,8,9,9a-decahydro-1H-2-benzazepine;

trans-dl-5a-phenyl-2,3,4,5,5a,6,7,8,9,9a-decahydro-1H-3-benzazepine;

trans-dl-5a-(3-methoxyphenyl)-2,3,4,5,5a,6,7,8,9,9a-decahydro-1H-2-benzazepine;

trans-dl-5a-(3-methoxyphenyl)-2,3,4,5,5a,6,7,8,9,9a-decahydro-1H-3-benzazepine;

trans-dl-5a-(3-ethoxyphenyl)-2,3,4,5,5a,6,7,8,9,9a-decahydro-1H-2-benzazepine; and related compounds.

With the N-unsubstituted benzazepine derivatives thus formed, the preparation of other compounds of the invention is relatively simple. Normal alkylation or acylation of such N-unsubstituted benzazepine derivatives provide, either directly, or in the case of N-acyl derivatives, after further modification, compounds of the invention wherein $R_1$ is other than hydrogen. For example, a benzazepine derivative such as trans-dl-5a-(3-n-propoxyphenyl)-2,3,4,5,5a,6,7,8,9,9a-decahydro-1H-2-benzazepine can be alkylated with essentially any alkylating agent of the formula $R_1$-B, wherein $R_1$ and B have the above-defined meanings. One such alkylation involves reacting the above-named benzazepine derivative with allyl bromide, in the presence of a base such as sodium bicarbonate and a solvent such as acetone, dimethylformamide, or the like, to provide, after normal isolation and purification, the corresponding N-allyl benzazepine derivative, for example trans-dl-5a-(3-n-propoxyphenyl)-2-allyl-2,3,4,5,5a,6,7,8,9,9a-decahydro-1H-2-benzazepine.

The N-unsubstituted benzazepine derivatives can alternatively be acylated at the N-position to provide the corresponding N-acylated benzazepine derivatives, which, being important intermediates, form a further embodiment of this invention. Reduction of the acyl carbonyl group of such derivatives provides the pharmacologically useful drugs of the invention.

The N-acylated benzazepines comprehended by this invention have the above generalized formula wherein $R_1$ is

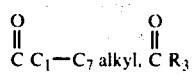

in which R₃ has the above-defined meaning, and

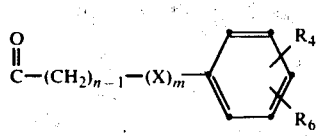

in which n, m, X, R₄ and R₅ are as defined above. Such N-acylated benzazepines are prepared by reacting an N-unsubstituted benzazepine with an acylating agent. Typical acylating agents include acid halides such as acid chlorides and acid bromides, as well as acid anhydrides, including mixed acid anhydrides. Commonly utilized acylating agents include acetyl chloride, pentanoyl bromide, benzoyl chloride, phenylacetyl chloride, phenoxyacetyl chloride, cyclopropylcarbonyl chloride, acetic anhydride, formic acetic anhydride, 3-methylphenylthioacetyl chloride, 3-benzoylpropionyl bromide, and the like. The acylation reaction typically is carried out by mixing about equimolar quantities of the N-unsubstituted benzazepine derivative and the acylating agent in a solvent such as acetone, benzene, or ethyl acetate, and in the presence of a base such as potassium carbonate or pyridine to act as an acid scavenger. The acylated product, a trans-dl-5a-aryl-2-acylated-2,3,4,5,5a,6,7,8,9,9a-decahydro-1H-2-benzazepine or a trans-dl-5a-aryl-3-acylated-2,3,4,5,5a,6,7,8,9-,9a-decahydro-1H-3-benzazepine, following normal isolation and purification if required, is next subjected to reduction, for example by reaction with lithium aluminum hydride, thereby converting the N-acylated benzazepine derivative to the corresponding N-alkylated benzazepine derivative contemplated by this invention. For example, a compound such as trans-dl-5a-phenyl-3-[3-(3,5-dibromophenylthio)propanoyl]-2,3,4,5,6,7,8,9,9a-decahydro-1H-3-benzazepine can be reduced by reaction with lithium aluminum hydride to provide trans-dl-5a-phenyl-3-[3-(3,5-dibromophenylthio)propyl]-2,3,4,5,5a,6,7,8,9,9a-decahydro-1H-3-benzazepine, a valuable pharmacological drug.

It should be noted that a number of the benzazepine derivatives of this invention, in addition to being useful drugs, are useful also as intermediates and are readily converted to other benzazepine derivatives of the invention. For example, those benzazepine derivatives having a 5a-phenyl group which is substituted at the 3-position by a methoxy group are readily demethylated to provide the corresponding hydroxyphenyl substituted benzazepine derivative. Such demethylation can be accomplished for example by reaction of the 5a-(3-methoxyphenyl)benzazepine derivative with 48 percent aqueous hydrobromic acid in acetic acid. For example, trans-dl-5a-(3-methoxyphenyl)-3-(5-hexenyl)-2,3,4,5,5a,6,7,8,9,9a-decahydro-1H-3-benzazepine can be reacted with excess 48 percent hydrobromic acid in acetic acid to provide, following normal isolation and purification if required, trans-dl-5a-(3-hydroxyphenyl)-3-(5-hexenyl)-2,3,4,5,5a,6,7,8,9,9a-decahydro-1H-3-benzazepine.

Such 5a-(3-hydroxyphenyl)-benzazepine derivatives are useful drugs, and additionally can be acylated to provide 5a-(3-alkanoyloxyphenyl)-benzazepine derivatives which are valuable drugs. A compound such as trans-dl-5a-(3-hydroxyphenyl)-3-(3-hydroxy-3-phenyl)-propyl-2,3,4,5,5a,6,7,8,9,9a-decahydro-1H-3-benzazepine can be reacted with about one molar quantity of acetyl chloride or acetic anhydride in the presence of a base such as triethylamine to provide, following isolation and further purification if needed, trans-dl-5a-(3-acetoxyphenyl)-3-(3-hydroxy-3-phenyl)propyl-2,3,4,5,5a,6,7,8,9,9a-decahydro-1H-3-benzazepine.

As hereinbefore pointed out, this invention contemplates, in addition to benzazepine derivatives as the free base, the non-toxic pharmaceutically acceptable acid addition salts thereof. Such salts are often preferred since they customarily exist as highly crystalline, easily purifiable, solids. Such salts also are easily formulated for convenient administration, as will be described hereinbelow. The non-toxic pharmaceutically acceptable acid addition salts of the benzazepine derivatives are prepared by reaction of such benzazepine derivative with an equimolar quantity or an excess of any of a number of common inorganic and organic acids. Inorganic acids routinely utilized to form such salts include hydrohalides such as hydrochloric, hydrobromic and hydroiodic acid, as well as phosphoric, nitric, sulfuric, perchloric, boric, and related acids. Preferred organic acids commonly used include acetic, propionic, maleic, succinic, palmitic, stearic, benzoic, adipic, picric, paratoluenesulfonic, and related organic acids. A typical method for preparing a non-toxic pharmaceutically acceptable acid addition salt comprises dissolving a benzazepine derivative such as trans-dl-5a-(3-hydroxyphenyl)-2-cyclohexylmethyl-2,3,4,5,5a,6,7,8,9,9a-decahydro-1H-2-benzazepine, as the free base, in an organic solvent such as acetone or diethyl ether, and then adding a suitable acid, for instance hydrogen bromide gas, thereby forming the corresponding salt, which normally is insoluble in such organic solvents and thus crystallizes out of solution and is readily recovered by filtration. Such salts are then further purified by recrystallization from solvents such as ethanol or a mixture of ethanol and water. The acid addition salts encompassed by this invention are systematically named according to the IUPAC system, by dropping the "e" of benzazepine and adding "ium", followed by the name of the salt forming acid. For example, a typical hydrogen iodide salt is named as trans-dl-5a-phenyl-2-methyl-2,3,4,5,5a,6,7,8,9,9a-decahydro-1H-2-benzazepinium iodide.

In an effort to more fully illustrate the scope of this invention, the following table is presented listing representative compounds prepared by the above-described processes and having the following generalized formula:

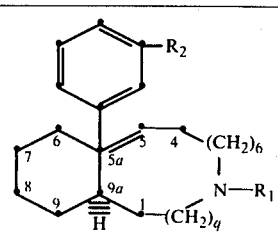

| q | y | R₁ | R₂ |
|---|---|---|---|
| 1 | 0 | CH₃ | H |
| 1 | 0 | CH₂CH₃ | OCH₃ |
| 1 | 0 | CH₂CH₂CH₃ | OCH₂CH₃ |
| 1 | 0 | CH₂CH(CH₃)₂ | OCOCH₃ |

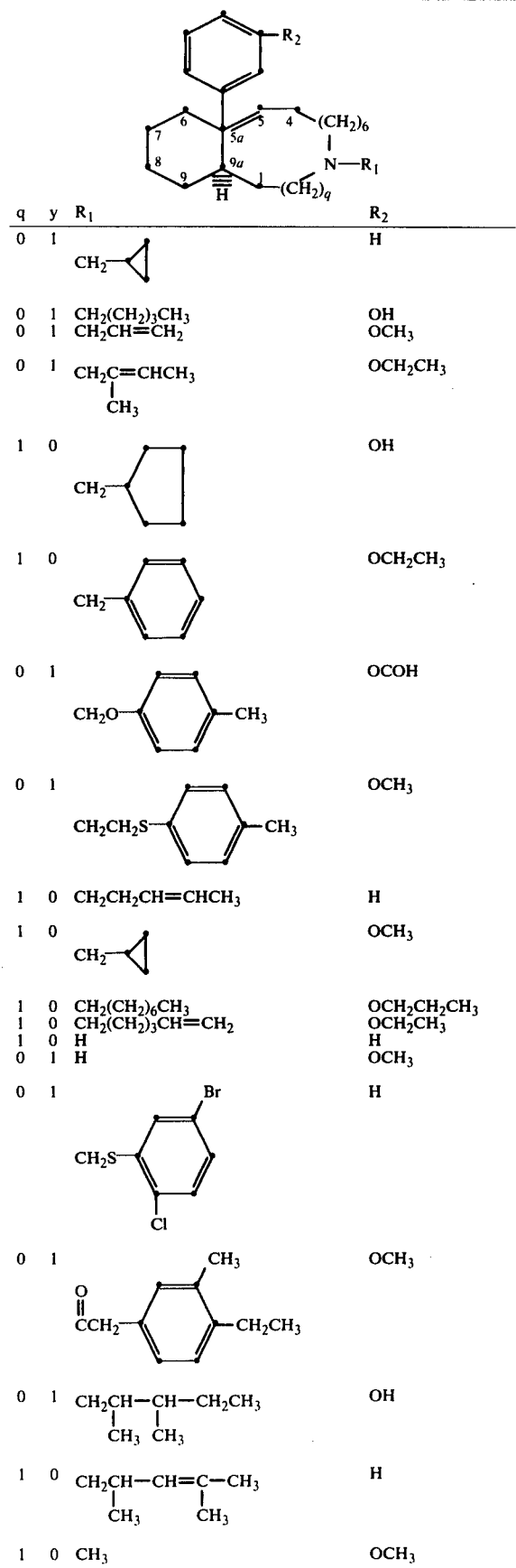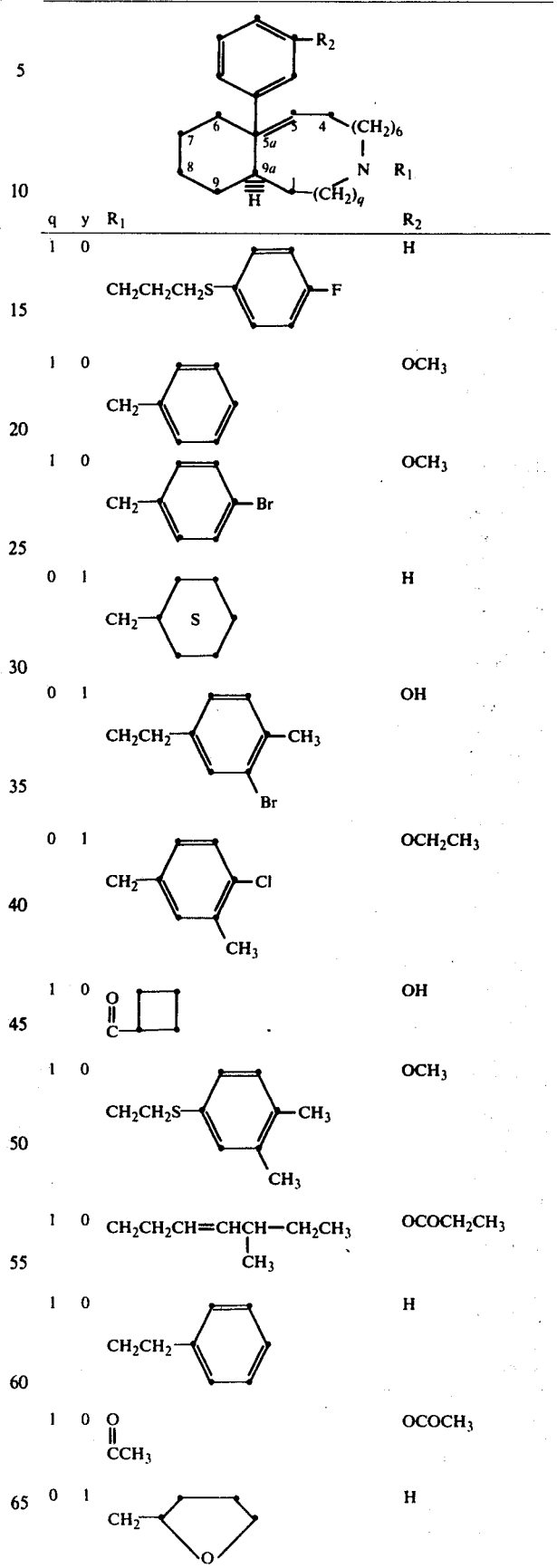

-continued

| q | y | R$_1$ | R$_2$ |
|---|---|-------|-------|
| 1 | 0 | CH$_2$—[furan] | OCH$_3$ |
| 1 | 0 | CH$_2$—[furan] | OCH(CH$_3$)$_2$ |
| 1 | 0 | CH$_2$—[furan] | OCHOCH$_2$CH$_3$ |

Additional compounds comprehended by the invention include:

trans-dl-5a-phenyl-2-ethyl-2,3,4,5,5a,6,7,8,9,9a-decahydro-1H-2-benzazepinium acetate;

trans-dl-5a-(3-methoxyphenyl)-3-isobutyl-2,3,4,5,5a,6,7,8,9,9a-decahydro-1H-3-benzazepinium phosphate;

trans-dl-5a-(3-acetoxyphenyl)-3-allyl-2,3,4,5,5a,6,7,8,9,9a-decahydro-1H-3-benzazepinium iodide;

trans-dl-5a-(3-hydroxyphenyl)-3-cyclopropylmethyl-2,3,4,5,5a,6,7,8,9,9a-decahydro-1H-3-benzazepinium bromide;

trans-dl-5a-phenyl-2-(2-benzoylethyl)-2,3,4,5,5a,6,7,8,9,9a-decahydro-1H-2-benzazepinium succinate;

trans-dl-5a-phenyl-2-(3-hydroxy-3-phenyl)propyl-2,3,4,5,5a,6,7,8,9,9a-decahydro-1H-2-benzazepinium tartrate; and the like.

The following detailed examples are provided by way of illustration of various aspects of this invention, but are in no way to be construed as limiting.

EXAMPLE 1

Following the procedure of Gray and Djerassi, J. Org. Chem., 35, 758, (1970), 154.1 g. of 2-(3-methoxyphenyl) cyclohexanone was added in dropwise fashion to a mixture of 73.5 g. of sodium hydride in 400 ml. of benzene (the sodium hydride was prepared by washing a 50 percent solution of sodium hydride in mineral oil with two 100 ml. portions of anhydrous benzene). A nitrogen atmosphere was maintained above the reaction mixture which was stirred and heated at reflux for 40 hours. Then while still at reflux temperature, 145.6 g. of 1-diethylamino-3-butanone in 50 ml. of anhydrous benzene was added to the reaction mixture in dropwise fashion. The resulting mixture was heated at reflux for an additional three hours and was then cooled, after which 100 ml. of water was added slowly. The reaction mixture was next diluted with both water and benzene. The benzene layer was separated and washed with water until the water washes were neutral to litmus. The benzene layer was dried and the benzene removed therefrom by evaporation. The resulting residue was subjected to distillation in vacuo using a Vigreux column. Fractions boiling in the range 165°–230° C. at 0.15 torr were collected and redistilled. 10-(3-Methoxyphenyl)-Δ$^1$-2-octalone, formed in the above reaction, distilled in the range 170°–6° C. at 0.1 torr (yield 62 g). Analysis; Calc. C, 79.65; H, 7.86; Found C, 79.42; H, 8.06.

EXAMPLE 2

A 5-liter three-neck flask set up with stirrer, dropping funnel and inlet tube was chilled in a dry-ice-acetone bath. 1620 ml. of anhydrous ammonia were condensed in the flask to which were added 15.67 g. of lithium over a half-hour period. A solution of 30.7 g. of 10-(3-methoxyphenyl)-Δ$^1$-2-octalone in 1 liter of ether was added to the solution of lithium in liquid ammonia while cooling with a dry ice-acetone bath. The solution was stirred two hours at the same temperature. 250 ml. of methanol were then added in dropwise fashion. After the completion of the addition of the methanol, the reaction mixture was allowed to come to ambient temperature whereat the ammonia volatilized. 1 liter of water was added. The organic layer was separated and washed successively with 1N aqueous hydrochloric acid and water. The organic layer was dried and the solvent removed therefrom by evaporation. The residue containing the mixture of trans-dl-4a-(3-methoxyphenyl)-2-decalone and the corresponding secondary alcohol was dissolved in 2 l. of acetone. 38 ml. of a Jones reagent (prepared by dissolving 13.36 g. of chromium trioxide in 11.5 ml. of 18 M aqueous sulfuric acid and then diluting the resulting solution to 50 ml. with water) was added in dropwise fashion with stirring. The reaction mixture was stirred for two and one-half minutes and then poured into a saturated aqueous sodium chloride solution. The organic layer was separated, and the organic solvents were evaporated therefrom in vacuo. The residue, comprising trans-dl-5a-(3-methoxyphenyl)-2-decalone, was dissolved in 3 l. of ether and the ethereal solution was washed twice with water and then dried. Removal of the ether by evaporation yielded a residue of the decalone which was purified by distillation. Fractions boiling in the range 164°–184° C. at 0.05 torr weighing 30 gms. were collected and redistilled. The fraction boiling in the range 155°–169° C. at a pressure 0.1 torr weighing 21 g. was collected. The product appeared to be better than 90 percent pure trans-dl-4a-(3-methoxyphenyl)-2-decalone. Analysis calc. C, 79.03; H, 8.58; Found C, 78.91; H, 8.50. Molecular weight by mass spectrograph: calculated 258, found 258.36.

EXAMPLE 3

The following reactants were mixed together in a 500 ml. 3-neck flask equipped with stirrer and condenser; 19.5 g. of trans-dl-4a-(3-methoxyphenyl)-2-decalone; 19.9 g. of hydroxylamine hydrochloride, 98 ml. of pyridine, and 98 ml. of anhydrous ethanol. The reaction mixture was heated at refluxing temperature for four hours and then cooled. The volatile constituents were removed by evaporation. The residue comprising the oxime of trans-dl-4a-(3-methoxyphenyl)-2-decalone was dissolved in a 1:1 mixture of ethyl acetate and ether. The resulting organic solution was washed three times with 500 ml. portions of water and then dried. Evaporation of the solvent yielded 21 g. of the oxime of trans-dl-4a-(3-methoxyphenyl)-2-decalone. m.p. 117°–119.5° C.

Analysis; Calc., C, 74.69; H, 8.48; N, 5.12; Found; C, 74.87; H, 8.70; N, 5.11.

EXAMPLE 4

A reaction mixture was prepared containing 21 g. of trans-dl-4a-(3-methoxyphenyl)-2-decalone oxime and 665 g. of polyphosphoric acid. The mixture was heated at 128° C. for 30 minutes while being stirred vigorously. The reaction mixture was then poured into two liters of an ice-water mixture, also with rapid stirring. The aqueous mixture was extracted with 2 l. of a 1:1 ether-ethyl acetate solvent mixture. The organic layer was separated, washed three times with one liter portions of water and dried. Evaporation of the solvent yielded a mixture of trans-dl-5a-(3-methoxyphenyl)-3-oxo-2,3,4,5,5a,6,7,8,9,9a-decahydro-1H-2-benzazepine and the corresponding 2-oxo-decahydro-1H-3-benzazepine derivative, yield = 13.5 g.

EXAMPLE 5

A solution of 13.5 g. of the mixture of oxo-decahydrobenzazepines from Example 4 in 70 ml. of toluene was added in dropwise fashion to a suspension of 3 g. of sodamide in 70 ml. of toluene in a 500 ml. three neck flask equipped with stirrer, condenser, thermometer, and inlet tube. The toluene was heated to reflux. Refluxing was continued for another four hours after which time the reaction mixture was cooled to ambient temperature. A solution of 7.7 g. of methyl iodide in 70 ml. of toluene was next added in dropwise fashion. This new reaction mixture was refluxed for an additional two hours. More toluene was then added, followed by water in dropwise fashion. The organic layer was separated, washed three times with 500 ml. portions of water and then dried. Evaporation of the solvents yielded 15 g. of a mixture of trans-dl-5a-(3-methoxyphenyl)-2-methyl-3-oxo-2,3,4,5,5a,6,7,8,9,9a-decahydro-1H-2-benzazepine and trans-dl-5a-(3-methoxyphenyl)-3-methyl-2-oxo-2,3,4,5,5a,6,7,8,9,9a-decahydro-1H-3-benzazepine formed in the above alkylation. NMR indicated that the isomer mixture was about a 45-55 mixture of the two named components.

EXAMPLE 6

A solution was prepared containing 1.2 g. of the mixture of N-methyl oxo decahydro benzazepines from Example 5 in 25 ml. of anhydrous tetrahydrofurane (THF). This solution was added to a suspension of 0.5 g. of lithium aluminum hydride in 100 ml. of anhydrous THF in a 250 ml. of three-neck flask equipped with stirrer and condenser. After the addition was completed, the reaction mixture was heated to refluxing temperature for about four hours. The progress of reaction was followed by thin-layer chromatography on silica using a 90 L percent ethyl acetate-10 percent ethanol solvent system. When TLC showed the reduction to be substantially complete, the reaction mixture was worked up in accordance with standard procedures including the addition of 20 ml. of ethyl acetate to decompose excess LiAlH$_4$ and sufficient ammonium chloride to precipitate inorganic salts present. The precipitated salts were separated by filtration and the filter cake was washed thoroughly. The organic layer and washes were combined and the combined organic solution evaporated to dryness in vacuo. The residue, containing a mixture of trans-dl-5a-(3-methoxyphenyl)-2-methyl-2,3,4,5,5a,6,7,8,9,9a-decahydro-1H-2-benzazepine and trans-d-5a-(3-methoxyphenyl)-3-methyl-2,3,4,5,5a,6,7,8,9,9a-decahydro-1H-3-benzazepine formed in the above reduction, was dissolved in ether and the ethereal layer washed with water. The ethereal layer was separated and the ether removed by evaporation. The residue was then dissolved in 15 percent aqueous hydrochloric acid and the acidic solution washed with ether. The acidic layer was made basic with concentrated ammonium hydroxide and the mixture of N-methyl decahydro benzazepines, being insoluble in the alkaline solution, separated and was extracted into ether. The ether layer was separated, washed with water, and dried. Evaporation of the ether to dryness yielded about 0.7 g. of the above mixture of N-methyl decahydro benzazepines.

A repeat of the above reaction using 12.5 g. of the mixture of amides and 5.0 g. of lithium aluminum hydride yielded 7.55 g. of the amine mixture. Vacuum distillation of the mixture yielded a purified fraction boiling in the range 164°-7° C. at 0.12 torr. Analysis; Calc.: C, 79.07; H, 9.95; N, 5.12; Found; C, 79.09; H, 9.66; N, 5.14.

A solution was prepared containing 9.25 g. of the mixture of trans-dl-N-methyl-5a-(3-m-methoxyphenyl)-1H-decahydro-2 and 3-benzazepines in 1000 ml. of ether. The ethereal solution was saturated with gaseous hydrogen bromide, thus forming the hydrobromide salts. An insoluble hydrobromide salt precipitated and was separated by filtration. The filter cake was washed with ether and then dissolved in 80 ml. of anhydrous ethanol. The hydrobromide salt of one isomeric N-methyl decahydro benzazepine (denominated for clarity as isomer A) crystallized and the crystals separated. After a second recrystallization from anhydrous ethanol, the salt melted at 229°-231° C. Isomer A was tentatively assigned the structure trans-dl-5a-(3-methoxyphenyl)-2-methyl-2,3,4,5,5a,6,7,8,9a-decahydro-1H-2-benzazepinium bromide.

The filtrate containing the hydrobromide salt of isomer B (tentatively assigned the structure trans-dl-5a-(3-methoxyphenyl)-3-methyl-2,3,4,5,5a,6,7,8,9,9a-decahydro-1H-3-benzazepine was evaporated to dryness and the residue treated with an excess of 10 percent aqueous sodium hydroxide. The free base thus formed, being insoluble in the alkaline aqueous solution, separated and was extracted into ether. The ethereal solution was washed with water and dried. Evaporation of the ethereal solution to dryness yielded 4.1 g. of isomer B free base as a residue. The residue was dissolved in 170 ml. of anhydrous ethanol and 3.4 g. of picric acid was added. The picrate salt of isomer B precipitated and was collected by filtration (yield about 5 g.). Recrystallization of the picrate from anhydrous ethanol yielded 4.0 g. of trans-dl-5a-(3-methoxyphenyl)-3-methyl-2,3,4,5,5a,6,7,8,9,9a-decahydro-1H-3-benzazepinium picrate. M.P. 148°-150° C.

The picrate salt of isomer B was dissolved in aqueous alkali thus forming isomer B as the free base. The free base, being insoluble in the aqueous alkaline solution, precipitated and was extracted into ether. The ether solution was washed with water and then dried. A solution of hydrogen bromide in ether was added until a positive congo red reaction was obtained. The insoluble hydrobromide salt thus formed was separated by decantation and washed with ether. The washed residue was dissolved in about 100 ml. of ethyl acetate to which a small amount of anhydrous ethanol was added. Isomer B hydrobromide crystallized from this solvent mixture and the crystals were separated by filtration. A yield of about 1.7 g. of trans-dl-5a-(3-methoxyphenyl)-3-methyl-2,3,4,5,5a,6,7,8,9,9a-decahydro-1H-3-benzazepinium bromide melting at 188°–189° C. was obtained.

EXAMPLE 7

400 mg. of isomer A (obtained from the hydrobromide salt of Example 6 by dissolving the hydrobromide salt of isomer A in aqueous alkali and extracting the insoluble free base in ether followed by evaporation of the ether), was refluxed for 15 hours in a mixture of 7 ml. of 48% aqueous hydrogen bromide in 7 ml. of acetic acid. The reaction mixture was diluted with water, and ice was added. The pH of the solution was adjusted to 10.2 using 50 percent aqueous sodium hydroxide. The free base of the 3-hydroxy compound derived from isomer A (ie. trans-dl-5a-(3-hydroxyphenyl)-2-methyl-2,3,4,5,5a,6,7,8,9,9a-decahydro-1H-2-benzazepine), being insoluble in the alkaline aqueous layer, separated and was extracted into ether. The ether layer was separated, washed with water, and dried. Evaporation of the ether in vacuo yielded an oil comprising a purified compound which crystallized upon the addition of a small amount of ethyl acetate. The crystals were separated by filtration and recrystallized from ethyl acetate to yield about 0.252 g. of trans-dl-5a-(3-hydroxyphenyl)-2-methyl-2,3,4,5,5a,6,7,8,9,9a-decahydro-1H-2-benzazepine. M.P. 138°–140° C.

EXAMPLE 8

One-half gram of trans-dl-5a-(3-methoxyphenyl)-3-methyl-2,3,4,5,5a,6,7,8,9,9a-decahydro-1H-3-benzazepinium bromide was demethylated with 50 percent HBr-acetic acid by the procedure of Example 7 to yield trans-dl-5a-(3-hydroxyphenyl)-3-methyl-2,3,4,5,5a,6,7,8,9,9a-decahydro-1H-3-benzazepine; yield 240 mg. The compound was purified by reaction with maleic acid to form trans-dl-5a-(3-hydroxyphenyl)-3-methyl-2,3,4,5,5a,6,7,8,9,9a-decahydro-1H-3-benzazepinium maleate. M.P. 168°–171° C.

Analysis: Calc.: C, 78.72; H, 9.71; N, 5.40; Found: C, 78.94; H, 9.47; N, 5.12.

As previously stated, the compounds of this invention are analgesic agonists and are capable of producing profound, opiate-like analgesia in mammals. The compounds demonstrate their analgesic agonist activity in the mouse writhing test and in the rat tail jerk assay, both standard assays for analgesic action. In the mouse writhing assay, the following E.D.$_{50}$'s (dose which decreases the number of writhing observations by 50 percent compared to controls) were obtained for the compounds for this invention as follows: The compound of Example 6 which was referred to as isomer A and tentatively assigned the structure of trans-dl-5a-(3-methoxyphenyl)-2-methyl-2,3,4,5,5a,6,7,8,9,9a-decahydro-1H-2-benzazepinium bromide $ED_{50}$ = 20 mg/kg subcutaneously;
35 mg/kg orally.

The compound of Example 6 which was referred to as isomer B and tentatively assigned the structure of trans-dl-5a-(3-methoxyphenyl)-3-methyl-2,3,4,5,5a,6,7,8,9,9a-decahydro-1H-3-benzazepinium bromide;

$ED_{50}$ = 20 mg/kg subcutaneously;
20 mg/kg orally.

The compound of Example 7 which was referred to as isomer A and tentatively assigned the structure of trans-dl-5a-(3-hydroxyphenyl)-2-methyl-2,3,4,5,5a,6,7,8,9,9a-decahydro-1H-2-benzazepine;

$ED_{50}$ = 10 mg/kg subcutaneously;
35 mg/kg orally.

The compound of Example 7 which was referred to as isomer B and tentatively assigned the structure of trans-dl-5a-(3-hydroxyphenyl)-3-methyl-2,3,4,5,5a,6,7,8,9,9a-decahydro-1H-3-benzazepine;

$ED_{50}$ = 4 mg/kg subcutaneously
20 mg/kg orally.

In the rat tail jerk assay, compounds of this invention demonstrated analgesic activity as follows: the compound believed to be trans-dl-5a-(3-methoxyphenyl)-3-methyl-2,3,4,5,5a,6,7,8,9,9a-decahydro-1H-3-benzazepinium bromide gave an increased reaction time at a 20 mg/kg dose level subcutaneously and at a dose level less than 50 mg/kg orally. The compound believed to be trans-dl-5a-(3-methoxyphenyl)-2-methyl-2,3,4,5,5a,6,7,8,9,9a-1H-2-benzazepinium bromide gave an increased reaction time at a 50 mg/kg dose level subcutaneously, and trans-dl-5a-(3-hydroxyphenyl)-2-methyl-2,3,4,5,5a,6,7,8,9,9a-1H-2-benzazepine at a dose level below 50 mg/kg subcutaneously.

The compounds of this invention can be employed to produce analgesia in mammals by administration via either the parenteral or oral route. For oral dosage, a suitable quantity of a pharmaceutically-acceptable salt of a pharmacologically active benzazepine having the above formula is mixed with starch or other suitable excipient, and the mixture placed in telescoping gelatin capsules each containing an analgesic dose of active ingredient. Similarly, the salt can be mixed with starch, a binder, or a lubricant, and the mixture compressed into tablets each containing a standard analgesic dose, typically ranging from about 0.5 to 5.0 mg/kg. The tablets may be scored if lower or divided dosages are to be used. With parenteral administration, the intramuscular or subcutaneous routes are preferred. For this purpose, aqueous solutions or suspensions are employed using a non-toxic pharmaceutically-acceptable salt of the benzazepine derivative of this invention in an amount sufficient for a human dose of about 0.1 to 2.0 mg/kg. In general, modes of administration and pharmaceutical forms found useful in the past for morphine, codeine, methadon, meperidine and other opiate-like analgesics can be adopted by those skilled in the art for the compounds of this invention.

I claim:
1. A compound of the formula

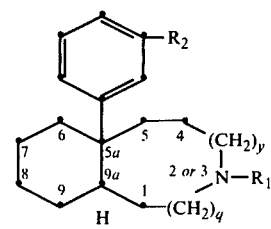

wherein:
one of y and q is zero and the other is 1;
$R_1$ is $C_1$-$C_8$ alkyl, $CH_2R_3$ or benzyl
wherein:
$R_3$ is $C_2$-$C_7$ alkenyl or $C_3$-$C_6$ cycloalkyl, $R_2$ is hydrogen, hydroxy, $C_1$-$C_3$ alkoxy; and the nontoxic pharmaceutically acceptable acid addition salts thereof.

2. A compound of claim 1 wherein q is zero and y is 1.

3. A compound of claim 2 wherein $R_2$ is hydroxy, or $C_1$-$C_3$ alkoxy.

4. A compound of claim 2 wherein $R_1$ is $C_1$-$C_8$ alkyl.

5. A compound of claim 4 wherein $R_1$ is methyl.

6. A compound of claim 2 wherein $R_1$ is $CH_2R_3$.

7. A compound of claim 6 wherein $R_1$ is allyl.

8. A compound of claim 6 wherein $R_1$ is cyclopropylmethyl.

9. A compound of claim 2 wherein $R_1$ is benzyl.

10. The compound of claim 9, said compound being trans-dl-5a-(3-methoxyphenyl)-2-benzyl-2,3,4,5,5a,6,7,8,9,9a-decahydro-1H-2-benzazepine.

11. A compound of claim 1 wherein y is 0 and q is 1.

12. A compound of claim 11 wherein $R_2$ is hydroxy, or $C_1$-$C_3$ alkoxy.

13. A compound of claim 11 wherein $R_1$ is $C_1$-$C_8$ alkyl.

14. A compound of claim 13 wherein $R_1$ is methyl.

15. The compound of claim 14, said compound being trans-dl-5a-(3-methoxyphenyl)-3-methyl-2,3,4,5,5a,6,7,8,9,9a-decahydro-1H-3-benzazepine.

16. A compound of claim 11 wherein $R_1$ is $CH_2R_3$.

17. A compound of claim 16 wherein $R_1$ is allyl.

18. A compound of claim 16 wherein $R_1$ is cyclopropylmethyl.

19. A compound of claim 11 wherein $R_1$ is benzyl.

20. The compound of claim 14, said compound being trans-dl-5a-(3-methoxyphenyl)-3-benzyl-2,3,4,5,5a,6,7,8,9,9a-decahydro-1H-3-benzazepine.

21. A compound of the formula

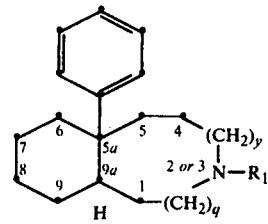

wherein:
one of y or q is zero and the other is 1;
$R_1$ is

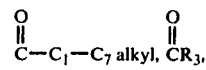

or benzoyl;
wherein:
$R_3$ is $C_2$-$C_7$ alkenyl, or $C_3$-$C_6$ cycloalkyl; and
$R_2$ is hydrogen, hydroxy, or $C_1$-$C_3$ alkoxy.

22. A compound of claim 21 wherein $R_1$ is

alkyl.

23. A compound of claim 21 wherein $R_1$ is

24. A compound of claim 23 wherein $R_3$ is $C_3$-$C_6$ cycloalkyl.

25. A compound of claim 21 wherein $R_1$ is benzoyl.

26. A compound of the formula

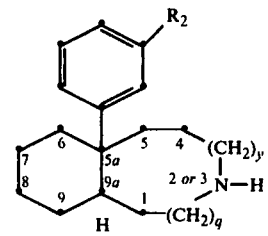

wherein:
one of y or q is zero and the other is 1; $R_2$ is hydrogen, hydroxy or $C_1$-$C_3$ alkoxy.

27. A compound of claim 26, wherein $R_2$ is hydrogen or $C_1$-$C_3$ alkoxy.

* * * * *